United States Patent [19]

Takasaki

[11] 3,950,222

[45] Apr. 13, 1976

[54] METHOD OF IMMOBILIZING ENZYMES TO MICROBIAL CELLS

[75] Inventor: Yoshiyuki Takasaki, Chiba, Japan

[73] Assignee: Agency of Industrial Science & Technology, Tokyo, Japan

[22] Filed: Mar. 1, 1974

[21] Appl. No.: 447,086

[30] Foreign Application Priority Data

Mar. 7, 1973  Japan............................... 48-27255

[52] U.S. Cl............... 195/68; 195/31 R; 195/31 F; 195/56; 195/59; 195/63; 195/64; 195/65; 195/111; 195/DIG. 11
[51] Int. Cl.$^2$ C12D 13/10; C07G 7/02; C12D 13/02
[58] Field of Search...... 195/63, 68, 65, 31 F, 31 R, 195/52, 56, 59, 111, DIG. 11

[56] References Cited
UNITED STATES PATENTS

| | | | |
|---|---|---|---|
| 3,553,310 | 1/1971 | Csizmas et al....................... | 195/63 |
| 3,779,869 | 12/1973 | Zienty.................................... | 195/68 |
| 3,843,442 | 10/1974 | Moskowitz......................... | 195/31 F |

OTHER PUBLICATIONS

Hough et al, *Nature* Vol. 235, (Feb., 1972), p. 389.

Zaborsky, *Immobilized Enzymes*, CRC Press, (1973), pp. 10, 11, 64.

Barker et al., "Enzyme Reactors for Industry," *Process Biochemistry*, Vol. 6, No. 10, pp. 11–13.

Emery et al, "Some Applications of Solid-Phase Enzymes in Biological Engineering," *Chem. Engineer, Birmingham University*, Vol. 22, No. 2, pp. 37–45.

*Primary Examiner*—A. Louis Monacell
*Assistant Examiner*—Thomas G. Wiseman
*Attorney, Agent, or Firm*—Ernest G. Montague; Karl F. Ross; Herbert Dubno

[57] ABSTRACT

Microorganic cells or microorganic cells which have undergone various forms of treatments, when treated with a reagent having two or more functional groups, give rise to microorganic cells having one of the functional groups of the said reagent chemically bonded thereto and also retaining a free functional group. Contact of an enzyme with the microorganic cells having a free functional group results in immobilization of the enzyme on the said cells.

6 Claims, No Drawings

METHOD OF IMMOBILIZING ENZYMES TO MICROBIAL CELLS

BACKGROUND OF THE INVENTION:

This invention relates to a method of immobilization enzymes and, more particularly, to a method for enzyme immobilization comprising the steps of treating microorganic cells or microorganic cells which have undergone various forms of treatments with a reagent having at least two functional groups and allowing an enzyme to react with resultant microorganic cells which have functional groups in a free state.

Immobilization (insolubilization) of enzymes has been attracting keen attention as a means for enabling enzyme reactions which have invariably been carried out in a batch operation to be accomplished in a continuous operation.

For example, a method whereby an enzyme is rendered insoluble in water by polymerizing the enzyme in the presence of a bifunctional reagent serving as an agent to bridge the enzyme molecules is disclosed in A. Schejter, A. Bar-Eli, Arch. Biochem. Biophys. Vol. 136, page 325 (1970) and a method whereby an enzyme is bonded to a water-insoluble carrier having an active group such as polyacrolein or polyurethane so as to produce an insolubilized enzyme has already been disclosed to the art.

The methods which have heretofore been disclosed have various disadvantages. For example, they entail high costs for the preparation of the insolubilized enzymes, fail to provide insolubilized enzymes with sufficiently high enzyme activity, allow enzymes to flow out of position in use because of insufficient immobilization, and necessitate development of different techniques to suit the immobilization of particular kinds of enzymes. These methods, therefore, have found very few commercial applications.

I have previously suggested a method whereby glucose isomerase-containing cells are subjected to heat treatment at 55° – 90°C to immobilize glucose isomerase within the cells. Since this method can economically produce the immobilized enzyme, it has already been adopted for commercial production of fructose from glucose. However, since no economical method has yet been made available for the immobilization of glucoamylase, it has heretofore been impossible to manufacture glucose continuously from starch (which term, for the purpose of the present specification, encompasses also liquefied starch, dextrin and the like) or produce fructose directly from starch by combining with the action of glucoamylase with that of glucose isomerase.

A primary object of the present invention is to provide a method of facilitating immobilization of enzymes on microorganic cells such as molds and actinomycetecells or products of treatments thereof.

SUMMARY OF THE INVENTION:

To accomplish the object described above, the method of this invention causes microorganic cells or products of treatments thereof to be treated with a reagent having two or more functional groups. It consequently creates microorganic cells having one of the functional groups of the reagent chemically bonded thereto and yet retaining a free functional group. An enzyme, when brought into contact with the resulting microorganic cells having a free functional group, is immobilized on the cells by the combination of the retained free functional group with the enzyme. Thus, the enzyme is immobilized on the microorganic cells by a cross-linking agent. If a glucoamylase is immobilized by this method on the cells containing glucose isomerase, therefore, fructose can be directly produced from starch by use of the cells thus prepared.

Other objects and characteristics of this invention will become apparent from the detailed description of the invention to be given herein below.

DETAILED DESCRIPTION OF THE INVENTION:

It has been found that glucoamylase, if immobilized economically, can be advantageously used for producing glucose from starch or, with glucose isomerase added to cooperate therewith, fructose directly from starch. The invention resides in the discovery that, when glucoamylase is bonded onto cells of a mold or an actinomycete with the aid of a reagent possessed of at least two functional groups, there can be produced a highly active immobilized enzyme in high yields.

The enzyme which can be immobilized by the method of this invention is not limited to glucoamylase. Various other enzymes such as α-amylase, β-amylase, isoamylase, pullulanase, invertase, galactosidase, cellulase, protease, lipase, glucose-oxidase and catalase can likewise be immobilized.

Not merely a single enzyme but two or more enzymes can be simultaneously immobilized. Such combinations are glucoamylase and glucose isomerase, β-amylase and isoamylase (or pullulanase), and α-amylase and glucoamylase, for example.

For the purpose of this immobilization, these enzymes are not required to be in a purified form but may be in a crude form containing extraneous proteins.

Molds and actinomycetes are particularly suitable microorganisms host cells for the purpose of immobilization of enzymes. This is because these microorganisms generally form relatively large pellets and, therefore, permit the preparation, recovery and other steps of handling immobilized enzymes to be carried out easily and economically. Other reasons are that these carriers are obtained very inexpensively, that they have appropriate degrees of specific gravity, that they are sufficiently dispersible in reaction liquids, and that they have large surface areas and therefore permit proportionately large quantities of enzymes to be bonded thereto.

Examples of the molds which are usable include those of genus Rhizopus, genus Aspergillus, and genus Penicillium. Examples of the actinomycetes which are also usable include those of genus Streptomyces and genus Actinomyces.

The host cells of these microorganisms may be those which occur as wastes from certain kinds of fermentation. In immobilizing glucoamylase, for example, if this enzyme is immobilized onto glucose isomerase-containing micororganic cells, the immobilized enzyme can be employed for producing fructose directly from starch.

The cells to be used for the immobilization of an enzyme are either subjected to heat treatment at a temperature of 50°C or over, generally in the range of from 50° to 100°C, for a period of from several minutes to several hours or treated with a dilute acid or alkali so as to have the autolytic activity of cells destroyed or to be freed of an easily separable cell component. If occasion demands, however, microorganic cells in a form still retaining physiological activity may be used, and cell walls of microorganisms may also be used.

Examples of the cross-linking reagents having at least two functional groups which are usable for this invention include tolylene diisocyanate, tolylene-2,4-diisocyanate, xylene diisocyanate, m-xylene-diisocyanate, epichlorohydrin, glutaraldehyde, phenol-disulfonyl-chloride, bis-diazobenzidine, toluene-2-isocyanate-4-isothiocyanate, nitrophenyl chloroacetate, 2-amino-4,6-dichloro-S-triazine and 2,4,6-trichloro-S-triazine. Particularly useful reagents are isocyanate compounds such as tolylene-2,4-diisocyanate.

The method for immobilizing an enzyme in accordance with the present invention will be described herein below by referring to a case wherein glucoamylase is immobilized on cells of a species of genus Streptomyces.

*Streptomyces albus* (ATCC 21132) is cultivated aerobically at 30°C for 30 hours in a medium containing 1% peptone, 1% glucose, 0.3% dibasic potassium phosphate and 0.1% magnesium sulfate. The cells are collected, suspended in water and subjected to heat treatment at 55° to 100°C. The cells are collected, washed, suspended in water (generally, by 0.5 – 5% on dry basis), combined with a water emulsion (about 20%) of tolylene diisocyanate and agitated.

The contact may be accomplished by adding the reagent to and stirring with the cells or by submerging the cells in the reagent. Generally, the duration of this contact ranges from several minutes to several hours at normal room temperature. At elevated temperatures, the period of this treatment may be shortened. On completion of the contact, the cells are washed as with water or a buffer solution and subsequently brought into contact with an enzyme.

Table 1 shows the effect of concentration of tolylene diisocyanate added into a definite amount of cells. Table 2 shows the effect of time of treatment of cells with tolylene diisocyanate. After the contact, the cells are collected and then washed thoroughly with water. Thus are obtained the cells of the Streptomyces having a free diisocyanate group retained thereon. Subsequently, a solution of glucoamylase is added to the resulting cells retaining the free isocyanate group and agitated for several minutes to several hours to ensure thorough contact. Table 3 shows the effect of time of incubation of cells having free isocyanate group with glucoamylase.

Table 1

Effect of concentration of tolylene diisocyanate

| Amount of tolylene diisocyanate (mg) | Amount of cells (mg) | Fixed glucoamylase (unit) |
|---|---|---|
| 0 | 20 | 5.6 |
| 10 | 20 | 8.2 |
| 20 | 20 | 44.2 |
| 40 | 20 | 162.2 |
| 60 | 20 | 198.4 |
| 80 | 20 | 181.4 |

One ml of cell suspension (20 mg) was added to 0 – 0.4 ml of 20% tolylene diisocyanate emulsified with water and incubated at 30°C by shaking. After 20 minutes, the cells were filtered and washed with distilled water. Thus obtained cells having free isocyanate group were added to 1 ml of glucoamylase solution (6845 units) from Aspergillus niger and incubated at 30°C for 120 minutes. The cells were collected and washed with distilled water.

Table 2

Effect of time of treatment of cells with tolylene diisocyanate

| Time of treatment (min.) | Fixed glucoamylase (unit) |
|---|---|
| 5 | 89.4 |
| 10 | 154.8 |
| 20 | 174.0 |
| 30 | 152.4 |
| 60 | 153.9 |

One ml of cell suspension (20 mg) was added to 0.3 ml of 20% tolylene diisocyanate emulsified with water, and incubated at 30°C by shaking. After indicated time intervals, the cells were filtered and washed with distilled water. Thus obtained cells having free isocyanate group were added to 1 ml of glucoamylase solution (6845 units) from Aspergillus niger and incubated for 120 minutes at 30°C. Then, the cells were filtered and washed with distilled water.

Table 3

Effect of time of incubation of cells having fee isocyanate group with glucoamylase.

| Time (min.) | Fixed glucoamylase (unit) |
|---|---|
| 0 | 3.5 |
| 10 | 42.3 |
| 30 | 87.5 |
| 120 | 184.2 |

One ml of cell suspension (20 mg) was added to 0.3 ml of 20% tolylene diisocyanate emulsified with water and incubated at 30°C by shaking. After 20 minutes, the cells were filtered and washed with distilled water. Thus obtained cells having free isocyanate group were added to 1 ml of glucoamylase solution (6845 units) and incubated at 30°C for indicated time intervals. Then the cells were filtered and washed with distilled water.

The contact may be carried out continuously by having the cells kept as a stationary phase. Thereafter, excess enzyme is recovered by means of filtration or centrifugation. The cells are washed thoroughly with water. Consequently, there are obtained cells on which glucoamylase is immobilized.

Although the preceding explanation has described a method whereby the immobilization is effected by treating the cells with a reagent and thereafter bringing the enzyme into contact with the cells, the immobilization of the enzyme to the cells may alternatively be carried out by immersing the cells in a solution containing the enzyme and subsequently treating them with a reagent added thereto.

As is clear from the explanation given above, this invention is directed to immobilizing an enzyme on microorganic cells by first converting the microorganic cells with a cross-linking agent into cells possessed of a free functional group and causing the enzyme to be bonded to the cells. By this method, therefore, various enzymes can readily be immobilized.

Further, when an enzyme is immobilized according to this invention on microorganic cells which already contain another enzyme, the use of the resulting microorganic cells enables an enzyme reaction which has heretofore required two steps of process to be accomplished in one step.

Microorganic cells are available inexpensively as compared with ion-exchange resins, cellulose and other carriers which are now in popular use. Therefore, microorganic cells having a free functional group retained therein can advantageously be employed for the seizure, recovery and removal of not merely enzymes but equally organic compounds such as proteins, amino acids and organic acids, inorganic compounds, metals, etc.

Now, preferred embodiments of this invention will be described. The examples shall be interpreted as illustrative and not in a limiting sense.

EXAMPLE 1:

Streptomyces albus (ATCC 21132) was inoculated to a liquid medium (pH 7.2) containing 0.5% of xylane, 4% of corn steep liquor and 0.024% of $CoCl_2.6H_2O$ and aerobically cultivated at 30°C for 24 hours. At the end of the culture, the microorganic cells were collected, washed with water and thereafter suspended in water and subjected to heat treatment at 65°C for 15 minutes.

To 2-ml portions of the resultant cell suspension were respectively added tolylene diisocyanate, xylene diisocyanate, epichlorohydrin and glutaraldehyde each in a volume of 0.2 ml. The mixture were stirred at 30°C for 1 hour. Consequently, there were obtained cells of Streptomyces albus having thereon tolylene diisocyanate, xylene diisocyanate, epochlorohydrin and glutaraldehyde respectively. The cells thus produced were found to possess free functional groups capable of bonding various enzyme proteins in high yields. To these cells of the Streptomyces having said free functional groups retained thereon, 1 ml (9200-units/ml) of glucoamylase produced by a genus Rhizopus was added and incubated at 30°C for 30 minutes. Thereafter, the cells were deprived of excess enzyme, washed thoroughly with water and analyzed to determine the quantity of glucoamylase bonded thereto. The results thus obtained are shown in Table 4.

Table 4

| Functional reagent | Glucoamylase immobilized (units) |
|---|---|
| Tolylene diisocyanate | 287.1 |
| Xylene diisocyanate | 188.8 |
| Epichlorohydrin | 165.5 |
| Glutaraldehyde | 20.4 |

The assay of glucoamylase was carried out in a water bath at 50°C in a mixture of 2% soluble starch, 0.05M acetate buffer and an adequate amount of the enzyme. For the assay of immobilized glucoamylase, the reaction was carried out by shaking.

One unit was defined as the enzyme amount which produces 1 mg of glucose per hour.

EXAMPLE 2:

A 2-ml portion of the cell suspension of the same Streptomyces as used in Example 1 was combined with 1 ml of 20% tolylene diisocyanate emulsified with water and incubated with stirring at 30°C for 30 minutes.

Consequently, there were obtained cells of Streptomyces having retained thereon a free isocyanate group.

The cells were subsequently washed thoroughly with water and thereafter held in contact with 1 ml of a commercially available invertase produced by Candida utilis at 30°C for 30 minutes. As a result, 30 units of the invertase was immobilized to the cells.

One unit of invertase was defined as the enzyme amount which produces reducing power corresponding to 1 mg glucose per hour at 30°C in a reaction mixture containing 0.1M sucrose, 0.05M acetate buffer (pH 4.5) and the enzyme.

EXAMPLE 3:

A 2-ml portion of the cells suspension of the same Streptomyces as used in Example 1 was combined with 1 ml of 20% tolylene diisocyanate emulsified with water and incubated at 30°C for 1 hour. Consequently, there were obtained cells of Streptomyces having retained thereon a free isocyanate group. Subsequently, the cells were held in contact with 1 ml of a commercially available malt $\beta$-amylase (508 units/ml) at 30°C for 30 minutes. The cells were filtered, washed to be deprived of excess enzyme and analyzed to determine the quantity of $\beta$-amylase immobilized thereto. The analysis showed that 80.5 units of $\beta$-amylase had been immobilized.

One unit of $\beta$-amylase was defined as the enzyme amount which produces 1 mg of maltose per hour at 37°C in a reaction mixture containing 2% soluble starch, 0.05M acetate buffer (pH 5.5) and the enzyme.

EXAMPLE 4:

Aspergillus niger was aerobically cultured in a medium containing 5% of sucrose, 1.5% of peptone, 0.5% of $K_2HPO_4$ and 0.25% of $MgSO_4.7H_2O$. The microorganic cells obtained were subjected to heat treatment at 60°C for 10 minutes. Subsequently, they were thoroughly washed with water and suspended in water. The cell suspension had a cell concentration of about 10 mg/ml.

A 2-ml of the cell suspension was combined with 1 ml of 20% tolylene diisocyanate emulsified with water and then incubated at 30°C for 1 hour. Consequently, there were obtained cells of Aspergillus niger having retained thereon a free isocyanate group. Subsequently, the cells were combined with 1 ml of Rhizopus glucoamylase (9200 units/ml) and incubated at 30°C for 30 minutes by shaking. The cells were thoroughly washed and then analyzed to determine the quantity of glucoamylase immobilized thereto. The analysis showed that 210 units of glucoamylase had been immobilized.

EXAMPLE 5:

Rhizopus oryzae was aerobically cultured in a medium containing 5% of sucrose, 1.5% of peptone, 0.5% of $K_2HPO_4$ and 0.25% of $MgSO_4.7H_2O$. The microorganic cells obtained were subjected to heat treatment at 60°C for 10 minutes. Subsequently, they were thoroughly washed with water and suspended in water. The cell suspension had a cell concentration of 10.0 mg/ml.

A 2-ml of the cell suspension was combined with 1 ml of 20% tolylene diisocyanate emulsified with water and then incubated at 30°C for 1 hour. Consequently, there were obtained cells of Rhizopus oryzae having retained thereon a free isocyanate group. Subsequently, the cells were combined with 1 ml of Rhizopus glucoamylase (9200 units/ml) and incubated at 30°C for 30 minutes by shaking. The cells were thoroughly washed and then analyzed to determine the quantity of glucoamylase immobilized thereto. The analysis showed that 120 units of glucoamylase had been immobilized.

What is claimed is:

1. A method for the immobilization of an enzyme on microorganic cells which comprises the steps of first treating said microorganic cells with a di-isocyanate reagent to produce microorganic cells each having a free functional group, and only thereafter reacting the microorganic cells having free functional groups thus obtained with an enzyme to immobilized said enzyme on said microorganic cells.

2. The method defined in claim 1, wherein the quantity of di-isocyanate reagents used is 1–4 times that of the microorganic cells.

3. A method of making microorganic immobilized-enzyme cells comprising the steps of:
   a. first reacting microorganic cells selected from the group which consists of mold and Actinomycetes cells with a di-isocyanate to affix said di-isocyanate with one of its functional groups to said cells while leaving another functional group of said di-isocyanate available for reaction; and
   b. only thereafter contacting the cells having said di-isocyanate affixed thereto with an enzyme reactive with said other group and selected from the group which consists of glucose isomerase, glucoamylase, $\alpha$-amylase, $\beta$-amylase, isoamylase, pullulanase, invertase, galactosidase, cellulase, lipase, protease, glucose oxidase and catalase to immobilize said enzyme on said cells.

4. The method defined in claims 3 wherein said cells are selected from the group which consists of Streptomyces, Aspergillus, Rhizopus and Penicillium and said di-isocyanate is selected from the group which consists of tolylene-di-isocyanate, tolylene-2, 4-di-isocyanate, xylene-di-isocyanate, m-xylene- di-isocyanate, and toluene-2-isocyanate-4-isothiocyanate.

5. The method defined in claim 3 wherein said di-isocyanate is tolylenediisocyanate.

6. The method defined in claim 5 wherein said cells are cells containing glucose isomerase and said enzyme is glucoamylase.

* * * * *